United States Patent [19]
Oshiro et al.

[11] Patent Number: 5,556,857
[45] Date of Patent: Sep. 17, 1996

[54] DISTURBANCE-OF-CONSCIOUSNESS IMPROVING AGENT

[75] Inventors: Yasuo Oshiro, Tokushima; Tatsuyoshi Tanaka, Tokushima-ken; Tetsuro Kikuchi, Tokushima; Katsura Tottori, Tokushima-ken, all of Japan

[73] Assignee: Otsuka Pharmaceutical Co., Ltd., Tokyo, Japan

[21] Appl. No.: 92,060

[22] Filed: Jul. 16, 1993

Related U.S. Application Data

[63] Continuation-in-part of Ser. No. 82,522, Jun. 25, 1993, which is a continuation of Ser. No. 878,515, May 5, 1992, abandoned.

[30] Foreign Application Priority Data

May 8, 1991 [JP] Japan .................. 3-102391
Jul. 17, 1992 [JP] Japan .................. 4-189785

[51] Int. Cl.⁶ .............. A61K 31/495; A61K 31/44; A61K 31/155; A61K 31/135
[52] U.S. Cl. .............. 514/253; 514/294; 514/634; 514/649; 544/363; 546/94; 564/230; 564/238; 564/240; 564/336
[58] Field of Search .............. 544/363; 514/253, 514/294, 634, 649; 546/94; 564/238, 240, 230, 336

[56] References Cited

U.S. PATENT DOCUMENTS

| | | | |
|---|---|---|---|
| 4,895,841 | 1/1990 | Sugimoto et al. | 514/212 |
| 5,100,901 | 3/1992 | Sugimoto et al. | 514/212 |

FOREIGN PATENT DOCUMENTS

| | | |
|---|---|---|
| 0226441 | 6/1987 | European Pat. Off. . |
| 296560 | 6/1988 | European Pat. Off. . |

OTHER PUBLICATIONS

Takano et al, CA 115:20831 (1991).
Takano et al, CA 115:159503 (1991).
Atami et al, CA 77:61842 (1972).
Pascaud et al, CA 118:116509 (1993).
Wettstein et al, CA 115:41909 (1991).
Merck Index, 9th Edition, 4414 (1976).
George R. Gewirtz et al, Neuropsychopharmacology 1994, vol. 10, No. 1, pp. 37–40.

*Primary Examiner*—Cecilia Tsang
*Attorney, Agent, or Firm*—Sughrue, Mion, Zinn, Macpeak & Seas

[57] ABSTRACT

The present invention provides a disturbance-of-consciousness improving agent which is a highly effective and quick remedy and which can be administered orally. The disturbance-of-consciousness improving agent of the invention contains a sigma receptor agonist compound as an active ingredient.

19 Claims, No Drawings

DISTURBANCE-OF-CONSCIOUSNESS IMPROVING AGENT

This is a continuation-in-part of the application Ser. No. 08/082,522 filed Jun. 25, 1993 which is a continuation of application No. 07/878,515 filed May 5, 1992, now abandoned.

The present invention relates to a disturbance-of-consciousness improving composition.

With the recent increase in the number of automobiles on the road, the incidence of traffic accidents and the number of consequent casualties have been on the steady increase to present a serious social problem. In traffic accidents many of the victims sustain a heavy blow on the head and a head injury. Many a victim, whose life is fortunately saved, suffers from sequela such as disorders of intellectual, motor and speech functions depending on the degree of impairment of brain function. In the worst cases, the outcome is the vegetative state or brain death. The damage to brain function is manifested first as disturbed consciousness.

Disturbances of consciousness are classified into those associated with some primary lesion of the brain substance inclusive of a head injury due to a traffic accident or the like and those arising from secondary causes such as metabolic derangement. Cerebrovascular disorders such as cerebral hemorrhage, cerebral thrombosis, cerebral infarction and subarachnoid hemorrhage, head injury, brain tumor, cerebral edema, encephalitis, meningitis, demyelinating disease, epilepsy, brain surgery, etc. can be mentioned as the primary lesions. Known as secondary lesions are metabolic disorders such as hypoglycemia, diabetic ketoacidosis and lacticemic acidosis, electrolyte disorders such as hyponatremia, hypernatremia, hypercalcemia and hypocalcemia, liver damage, hepatic coma, kidney disorder, hypoxia, hypertensive encephalopathy, severe anemia, circulatory failure, cardiac arrest, bypass surgery, alcoholism, poisoning by drugs such as hypnotics, psychotropic drugs and potassium cyanide, carbon monoxide poisoning, abnormal body temperature (hypothermia, hyperthermia), shock, etc. (Japanese Journal of Neuropsychopharmacology, 14(1):5–11, 1992).

Treatment of a disturbance of consciousness may be based on the dichotomy of the acute stage and the chronic stage. Any disturbance of consciousness in the acute stage is one of neuroemergencies and requires an immediate, pertinent treatment and this treatment is considered to be as important as to determine the prognosis of the case and the severity of sequelae. Moreover, an early recovery of consciousness enables a communication between the doctor and the patient which facilitates the doctor's assessment of the degree and extent of damage to brain function and, hence, enables him to design a more pertinent treatment modality. For a disturbance of consciousness in the chronic stage, it is sought to activate the residual intact neurons or suppressed brain functions to thereby treat the disturbance. In the acute stage, attempts should first be made to secure vital signs through airway maintenance, blood pressure management, artificial respiration, resuscitation, cardiac massage and other procedures. Then, treatments directed to primary and secondary causes are given. Subsequently, CT, roentgenography and a neurological examination for assessment of the degree of impaired consciousness, motor function and reflex function, inclusive of a questioning of the patient's attendants, are performed (Japanese Journal of Neuropsychopharmacology, 14(1):13–38, 1992).

The degree of consciousness disorder varies according to the degree of impairment of brain function. In Japan, the level of impaired consciousness is generally classified into coma, semicoma, stupor and lethargy according to the Japan Coma Scale (III-3 system). Aside from them, there also are special disturbances of consciousness such as confusion, delirium and akinetic mutism which develop especially in the chronic stage or as sequelae (Japanese Journal of Neuropsychopharmacology, 14(2):103–109, 1992).

It is generally considered that disturbances of consciousness occur as the reticular formation extending from the pons, which is the center of consciousness, to the brainstem tegmentum is injured either directly or indirectly. Although a fair amount of work has been done on the mechanisms involved in the onset of consciousness disorder and the neurotransmitters involved in this condition, the detailed picture has not been elucidated as yet (Brain and Nerve, 39(10):983–990, 1987).

It is generally acknowledged that the level of consciousness is determined by interactions of various kinds of neurons (neurotransmitters). As regards the acetylcholinergic nervous system, for instance, acetylcholine and physostigmine, an inhibitor of acetylcholine esterase, which are activators of the acetylcholinergic nervous system, are reportedly effective in improving disturbances of consciousness at low non-toxic doses. In the case of the dopaminergic nervous system, it has been reported that methamphetamine, a dopamine release accelerator, improves impaired consciousness, while haloperidol, a dopamine receptor antagonist, delays recovery from coma. As to the serotonergic nervous system, the serotonin receptor antagonist methysergide improves impaired consciousness. However, regarding the adrenergic or noradrenergic nervous system, no clear-cut information has been generated. From these circumstances, it is inferred that external stimuli such as head traumas inhibit the acetylcholinergic and dopaminergic nervous systems and, the other way round, stimulate the serotonergic nervous system, thus causing a decreased level of consciousness, i.e. coma state (Brain and Nerve, 39:983–990, 1987). The above may lead to the postulate that all of acetylcholine receptor agonists, dopamine receptor agonists and serotonin receptor antagonists would improve impaired consciousness. However, agents which directly act on the cerebral nervous system cannot be used liberally as therapeutic drugs off-hand. By way of illustration, acetylcholine and acetylcholine esterase inhibitors have serious side effects, and methamphetamine may produce an addictive behavior as well as schizophrenic responses such as hallucinations and delusion.

As therapeutic agents for impairment of consciousness, the lecithin cosynthetase preparation citicoline, the choline derivative meclofenoxate, and thyrotropin releasing hormone (TRF-T) have been approved for clinical use in the injection form. Citicoline and meclofenoxate have been used as ameliorative agents for impaired consciousness in the acute stage, while TRH-T has been used in the treatment of protracted disturbance of consciousness in the chronic stage with fixed symptoms (Japanese Journal of Neuropsychopharmacology, 2(2):113–119). However, these therapeutic drugs are not effective when given orally. Moreover, these therapeutic agents are not sufficiently effective in improving impaired consciousness and, therefore, the advent of more effective and immediately acting ameliorative agents for impaired consciousness has been awaited. Particularly for the treatment of disturbance of consciousness in the chronic stage, preparations for oral administration are demanded.

Since the existence of sigma receptors was first reported in 1976 (Journal of Pharmacology and Experimental Therapy, 197(1):517, 1976), their correlates with opiate receptors have been explored. It has been shown that sigma receptors are different from mu, kappa, delta or epsilon opiate receptors. As it was subsequently discovered that most antischizoprenic drugs including haloperidol have affinities for these receptors and that phencyclidine (PCP) having an affinity for sigma receptors induces schizophrenic responses such as hallucinations and delusion, studies on these receptors have so far been focused on their association with schizophrenia. Sigma receptors were initially identified with receptors of hallucinogenic, delusion-inducing phencyclidine (PCP) but subsequent studies revealed that PCP receptors and sigma receptors are independent receptors (pharmacological Review, 42(4):355–402).

It is well known that compounds having sigma receptor binding activity are useful as nonnarcotic analgesics, as prophylactic and therapeutic drugs for general neurological and/or psychiatric disorders such as depression, memory disorder and/or abnormal behaviors induced by antischizophrenic drugs, schizophrenia, Alzheimer's disease, Parkinson's disease and senile dementia, as therapeutic agents for general gastrointestinal dysfunction such as impaired peristalsis/motor activity, gastroesophageal/gastroduodenal reflux and gastric/gastroduodenal ulcer, and as diagnostic and therapeutic agents for psychoses (see J. Michael Waler et al., Pharmacological Reviews, 42(4):355–402, 1990; Francois J. Roman et al., Journal of Pharmacy and Pharmacology: 42:439–440, 1990).

Regarding such compounds having the potential to bind sigma receptors, the following information has further been made available. First, the involvement of them in the control of release of cerebral neurotransmitters has been suspected (European Journal of Pharmacology 138:447–449, 1987). There also are reports suggesting their involvement in muscle contraction (European Journal of Pharmacology, 139:125–128, 1987 and European Journal of Neuroscience, 9:3382–3391, 1989). The effect of such compounds on the gastrointestinal system (Gastroenterology, 97:76–82, 1986 and European Journal of Pharmacology Experimental Therapy, 255:1354–1359, 1990) has also been pointed out. Their involvement in motor function such as dystonia induced by antischizophrenic agents, e.g. haloperidol (Neurology, 38:961–965, 1988), was also suspected. Other reports suggest the involvement of such substances in the metabolic turnover of inositol phosphate (European Journal of Pharmacology Experimental Journal of Pharmacology, 139:399–400, 1989), in muscarinic cholinergic blocking activity (European Journal of Pharmacology Experimental Therapy, 254:952–956, 1990) or in antischizophrenic activity (Clinical Psychiatry, 33(2):125–131).

However, it has not been reported that compounds having sigma receptor agonistic activity have an ameliorative action on impairment of consciousness.

The inventors of the present invention did much research into such sigma receptor agonist compounds and found that these compounds have disturbance-of-consciousness improving activity which can hardly be predicted from the current knowledge of their pharmacologic actions and that they can be elaborated into useful disturbance-of-consciousness improving drugs suited for oral administration. The present invention has been conceived and developed on the basis of the above findings.

The present invention is, therefore, directed to a disturbance-of-consciousness improving composition characterized by comprising a sigma receptor agonist compound as an active ingredient.

As the sigma receptor agonist compound for use in accordance with the present invention, the hitherto-known compounds can be widely used. Such compounds include, for example, 3-methoxy-N-methylmorphinan (dextromethorphan) and the following four derivatives: benzmorphan derivatives of the general formula

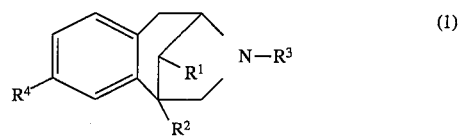

wherein $R^1$ and $R^2$ each represent hydrogen or lower alkyl; $R^3$ represents hydrogen, lower alkyl, lower alkenyl or cycloalkylmethyl; and $R^4$ represents hydroxy or lower alkoxy; guanidine derivatives of the general formula

wherein $R^5$ and $R^6$ each represent $C_4$ or higher alkyl, $C_{3-12}$ cycloalkyl, or $C_6$ or higher carbocyclic aryl; N-cycloalkylbenzylamine derivatives of the general formula

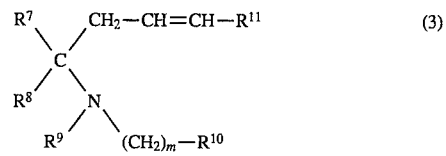

wherein $R^7$ represents phenyl which may be substituted by 1 to 3 members selected from halogen, lower alkyl, halo(lower)alkyl and lower alkoxy on the phenyl ring; $R^8$ represents lower alkyl; $R^9$ represents hydrogen or lower alkyl; $R^{10}$ represents cycloalkyl, which may be substituted by lower alkyl or phenyl on the cycloalkyl ring; $R^{11}$ represents phenyl which may be substituted by 1 to 3 members selected from halogen and lower alkoxy on the phenyl ring; and m is equal to 1 or 2; and carbostyril derivatives of the general formula

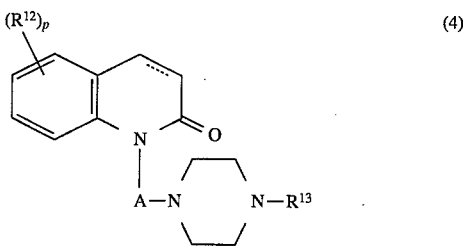

wherein $R^{12}$ represents hydroxy, lower alkoxy, lower alkyl, lower alkenyloxy, halogen, amino, lower alkanoylamino or lower alkylthio; $R^{13}$ represents phenyl which may be substituted by 1 or 2 members selected from halogen, lower alkoxy, lower alkyl, nitro, amino, lower alkanoylamino, hydroxy, cyano, phenyl-lower alkoxy and halo(lower) alkyl on the phenyl ring; A represents lower alkylene; p is equal to 1 or 2; and the carbon-carbon bond between the positions 3 and 4 of the carbostyril skeleton is a single or double bond.

Preferred examples of the above compounds include 2-allyl-5,9-dimethyl-2'-hydroxy-6,7-benzomorphan, 2-(3-methyl-2-butenyl)-5,9-dimethyl-2'-hydroxy-6,7-benzomorphan, 2-cyclopropylmethyl-5,9-dimethyl-2'-hydroxybenzomorphan, 2-methyl-5,9-dimethyl-2'-hydroxybenzomorphan, N,N'-di-(2-methylphenyl)guanidine, α-cinnamyl-N-cyclopropylmethyl-α-ethyl-N-methylbenzylamine, 5-methoxy-1-{3-[4-(3-chlorophenyl)-1-piperazinyl]propyl}-3,4-dihydrocarbostyril, 5-methoxy-1-{3-[4-(3-bromophenyl)-1-piperazinyl]propyl}-3,4-dihydrocarbostyril, 5-methoxy-1-{3-[4-(3-nitrophenyl)-1-piperazinyl]propyl}-3,4-dihydrocarbostyril, 5-ethoxy-1-{3-[4-(3-chlorophenyl)-1-piperazinyl]propyl}-3,4-dihydrocarbostyril, 5-chloro-1-{3-[4-(3-methoxyphenyl)-1-piperazinyl]propyl}-3,4-dihydrocarbostyril and 3-methoxy-N-methylmorphinan.

Specific examples of the groups represented by the symbols in the above general formulas (1) to (4) are as follows.

The lower alkyl group includes straight or branched alkyl groups containing 1 to 6 carbon atoms, such as methyl, ethyl, propyl, isopropyl, butyl, tert-butyl, pentyl and hexyl.

The lower alkenyl group includes straight or branched alkenyl groups containing 2 to 6 carbon atoms, such as vinyl, allyl, 2-butenyl, 3-butenyl, 1-methylallyl, 2-pentenyl, 2-hexenyl, 3-methyl-3-butenyl, 3-methyl-2-butenyl and 2,3-dimethyl-2-butenyl.

The cycloalkylmethyl group includes $C_{3-6}$ cycloalkylmethyl groups, such as cyclopropylmethyl, cyclobutylmethyl, cyclopentylmethyl and cyclohexylmethyl.

The lower alkoxy group includes straight or branched alkoxy groups containing 1 to 6 carbon atoms, such as methoxy, ethoxy, propoxy, isopropoxy, butoxy, tert-butoxy, pentyloxy and hexyloxy.

The $C_4$ or higher alkyl group includes straight or branched alkyl groups containing 4 to 12 carbon atoms, such as butyl, isobutyl, tert-butyl, amyl, hexol, octyl, nonyl, decyl, undecyl and dodecyl.

Examples of the $C_{3-12}$ cycloalkyl group include cyclopropyl, cyclopentyl, cyclohexyl, cycloheptyl, 1,4-methylenecyclohexyl, adamantyl, cyclopentylmethyl, cyclohexylmethyl, 1- or 2-cyclohexylethyl and 1-, 2- or 3-cyclohexylpropyl.

The $C_6$ or higher carbocyclic aryl group includes, for example, a carbocyclic aryl, alkanol or aralkyl group which contains 6 to 18 carbon atoms and 1 to 3 independent or condensed aromatic rings, such as phenyl, 2,3- or 4-tolyl, 3,5-dimethylphenyl, 2-, 3- or 4-ethylphenyl, 3,5-diethylphenyl, 3-methyl-5-ethylphenyl, 2-propylphenyl, naphthyl, 2-naphthyl and biphenyl. Examples also include those which have at least one substituent which is chemically and physiologically less active than guanidine. Such substituents include $C_{1-8}$ alkyl groups such as methyl and ethyl; halogen atoms such as fluorine, chlorine, bromine and iodine; nitro; azido; cyano; isocyanate; amino; lower alkylamino; di-lower alkylamino; trifluoromethyl; $C_{1-8}$ alkoxy groups such as methoxy, ethoxy and propoxy; $C_{1-8}$ alkanoyloxy groups such as acetoxy; acyloxy groups such as benzoxy; amido groups such as acetamido and N-ethyl acetamido; and carbamido groups such as carbamyl, N-methyl carbamyl and N,N'-dimethylcarbamyl.

The halo(lower)alkyl group includes straight or branched alkyl groups which contain 1 to 6 carbon atoms and 1 to 3 halogen atoms, such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 2,3-dichloropropyl, 1-chloro-2-fluoroethyl, 2,2,2-trifluoroethyl, 2,2,2-trichloroethyl, 3-chloropropyl, 3-fluoropropyl, 3,3,3-trichloropropyl, 4-chlorobutyl, 4-fluorobutyl, 4,4,4-trichlorobutyl, 5-chloropentyl, 5-bromohexyl, 6-chlorohexyl, 5,6-dichlorohexyl and 3-chloro-2-methylpropyl.

The phenyl group which may be substituted by 1 to 3 members selected from halogen, lower alkyl, halo(lower)alkyl and lower alkoxy on the phenyl ring includes phenyl and mono-, di- and tri-substituted phenyl groups in which each substituent on the phenyl ring is independently selected from the group consisting of halogen, $C_{1-6}$ straight or branched alkyl, $C_{1-6}$ straight or branched alkyl which has 1 to 3 halogens as substituent(s) and $C_{1-6}$ straight or branched alkoxy, such as 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl, 2-methoxy-3-chlorophenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3,4,5-trimethylphenyl, 3-chloro-4-methylphenyl, 3-methoxy-4-methyl-5-iodophenyl, 3,4-dimethoxy-5-bromophenyl, 3,5-diiodo-4-methoxyphenyl, 2-trifluoromethylphenyl, 3-trichloromethylphenyl and 4-(2,12,2-trifluoroethyl)phenyl.

The cycloalkyl group includes $C_{3-6}$ cycloalkyl groups, such as cyclopropyl, cyclobutyl, cyclopentyl and cyclohexyl.

The phenyl group which may be substituted by 1 to 3 members selected from halogen and lower alkoxy on the phenyl ring includes phenyl and mono-, di- and tri-substituted phenyl groups in which each substituent on the phenyl ring is independently selected from the group consisting of halogen and $C_{1-6}$ straight or branched alkoxy, such as 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 3,4,5-trimethoxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 3,4,5-trichlorophenyl and 2-methoxy-3-chlorophenyl.

The lower alkenyloxy group includes straight or branched alkenyloxy groups containing 2 to 6 carbon atoms, such as vinyloxy, allyloxy, 2-butenyloxy, 3-butenyloxy, 1-methylallyloxy, 2-pentenyloxy and 2-hexenyloxy.

The halogen includes fluorine, chlorine, bromine and iodine.

The lower alkanoylamino group includes $C_{1-6}$ straight or branched alkanoylamino groups, such as formylamino, acetylamino, propionylamino, butyrylamino, isobutyrylamino, pentanoylamino, tert-butylcarbonylamino and hexanoylamino.

The lower alkylthio group includes straight or branched alkylthio groups containing 1 to 6 carbon atoms, such as methylthio, ethylthio, propylthio, isopropylthio, butylthio, tert-butylthio, pentylthio and hexylthio.

The phenyl-lower alkoxy group includes phenylalkoxy groups in which the alkoxy moiety is straight or branched alkoxy containing 1 to 6 carbon atoms, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy and 2-methyl-3-phenylpropoxy.

The phenyl group which may be substituted by 1 or 2 members selected from halogen, lower alkoxy, lower alkyl, nitro, amino, lower alkanoylamino, hydroxy, cyano, phenyl-lower alkoxy and halo(lower)alkyl on the phenyl ring includes phenyl and mono- and di-substituted phenyl groups in which each substituent on the phenyl ring is independently selected from the group consisting of halogen, $C_{1-6}$ straight or branched alkoxy, $C_{1-6}$ straight or branched alkyl, nitro, amino, $C_{1-6}$ straight or branched alkanoylamino, hydroxy, cyano, phenylalkoxy in which the alkoxy moiety is $C_{1-6}$ straight or branched alkoxy, and $C_{1-6}$ straight or branched alkyl having 1 to 3 halogen atoms as substituent(s), such as 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-pentyloxyphenyl, 2,4-dimethoxyphenyl, 4-hexyloxyphenyl, 3,4-dimethoxyphenyl, 3-ethoxy-4-methoxyphenyl, 2,3-dimethoxyphenyl, 3,4-diethoxyphenyl, 2,5-dimethoxyphenyl, 2,6-dimethoxyphenyl, 3,5-dimethoxyphenyl, 3,4-dipentyloxyphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 3-iodophenyl, 4-iodophenyl, 3,4-dichlorophenyl, 3,5-dichlorophenyl, 2,6-dichlorophenyl, 2,3-dichlorophenyl, 2,4-dichlorophenyl, 3,4-difluorophenyl, 3,5-dibromophenyl, 2-methoxy-3-chlorophenyl, 2-methylphenyl, 3-methylphenyl, 4-methylphenyl, 2-ethylphenyl, 3-ethylphenyl, 4-ethylphenyl, 4-isopropylphenyl, 3-butylphenyl, 4-pentylphenyl, 4-hexylphenyl, 3,4-dimethylphenyl, 3,4-diethylphenyl, 2,4-dimethylphenyl, 2,5-dimethylphenyl, 2,6-dimethylphenyl, 3-chloro-4-methylphenyl, 2-trifluoromethylphenyl, 3-trifluoromethylphenyl, 4-trifluoromethylphenyl, 2-chloromethylphenyl, 3-(2-bromoethyl)phenyl, 4-(3,3,3-trichloropropyl)phenyl, 2-(4-chlorobutyl)phenyl, 3-(5-chloropentyl)phenyl, 4-(6-chlorohexyl)phenyl, 2-nitrophenyl, 3-nitrophenyl, 4-nitrophenyl, 3,4-dinitrophenyl, 3,4,5-trinitrophenyl, 2-aminophenyl, 3-aminophenyl, 4-aminophenyl, 2-formylaminophenyl, 3-acetylaminophenyl, 2-propionylaminophenyl, 4-butyrylaminophenyl, 3-pentanoylaminophenyl, 4-hexanoylaminophenyl, 2-acetylamino-4-methylphenyl, 4-acetylamino-3-methoxyphenyl, 2-hydroxyphenyl, 3-hydroxyphenyl, 4-hydroxyphenyl, 2,3-dihydroxyphenyl, 2,4,6-trihydroxyphenyl, 2-cyanophenyl, 3-cyanophenyl, 4-cyanophenyl, 3,4-dicyanophenyl, 2-benzyloxyphenyl, 3-(2-phenylethoxy)phenyl, 4-(1-phenylethoxy)phenyl, 2-(3-phenylpropoxy)phenyl, 3-(4-phenylbutoxy)phenyl, 4-(5-phenylpentyloxy)phenyl and 2-(6-phenylhexyloxy)phenyl.

The lower alkylene group includes straight or branched alkylene groups containing 1 to 6 carbon atoms, such as methylene, ethylene, trimethylene, 2-methyltrimethylene, 1-methyltrimethylene, tetramethylene, pentamethylene, hexamethylene, 2-ethylethylene and 2,2-dimethyltrimethylene.

The compounds of the foregoing general formulas (1) to (3) and 3-methoxy-N-methylmorphinan are known compounds, which are disclosed in publications such as U.S. Pat. No. 4,048,178, U.S. Pat. No. 4,709,094, Published European Patent Application No. 0362001A1, U.S. Pat. No. 2,676, 177, Japanese Examined Patent Publication No. 31664/1970, Japanese Unexamined Patent Publication No. 4176/1976, Japanese Unexamined Patent Publication No. 45075/1974, Japanese Examined Patent Publication No. 10469/1973 and Belgian Patent No. 611000 or which can be readily prepared by the processes described in the above publications.

The compounds represented by general formula (4) are novel compounds which are undisclosed in literature. The compounds of general formula (4) can be prepared by various processes, preferably, for example, by a process illustrated below in Process 1.

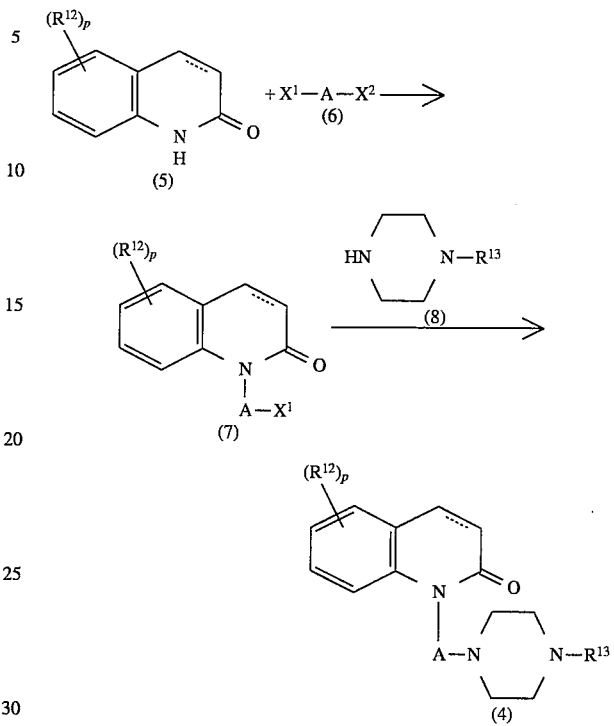

In the above reaction formula, $R^{12}$, $R^{13}$, A, p and the carbon-carbon bond between the positions 3 and 4 of the carbostyril skeleton are as defined above, and $X^1$ and $X^2$ are each a halogen atom.

In the above process 1, the compound of general formula (5) can readily be reacted with the compound of general formula (6) in an appropriate inert solvent in the presence of a hydrogen halide acceptor. The proportions of the compound of general formula (5) and the compound of general formula (6) are not critical but may be suitably selected from a wide range. Usually, the latter is used in an amount of not less than 1 mole, preferably 1 to 3 moles, per mole of the former. The hydrogen halide acceptor is, for example, an alkali metal such as sodium or potassium, an alkali metal amide such as sodium amide or potassium amide, or a sodium hydride. As the inert solvent, there may be mentioned, among others, aromatic hydrocarbons such as benzene, toluene and xylene, ethers such as tetrahydrofuran, dioxane and ethylene glycol dimethyl ether, dimethyl sulfoxide, dimethylformamide and hexamethylphosphoric triamide. Said reaction is carried out generally at 0° to 150° C., preferably at 0° to 100° C., and is generally complete in about 1 to about 12 hours. The compound of general formula (7) is thus obtained.

The reaction of the compound of general formula (7) with the compound of general formula (8) is carried out without using any solvent or in a conventional inert solvent at room temperature to 200° C., preferably 60° to 120° C. and is complete in about 1 to about 10 hours Usable as the inert solvent are the above-mentioned aromatic hydrocarbons, the above-mentioned ethers, lower alcohols such as methanol, ethanol and isopropanol, acetonitrile, dimethylformamide, dimethyl sulfoxide and like polar solvents. It is more advantageous to carry out the above reaction in the presence of a basic compound as a hydrogen halide acceptor. Examples of the basic compound are potassium carbonate, sodium carbonate, sodium hydroxide, sodium hydrogen carbonate, sodium amide, sodium hydride and like inorganic bases, triethylamine, tripropylamine, pyridine, 1,8-diazabicyclo [5.4.0]undecene-7 (DBU) and like organic bases. The above reaction may be accelerated, as necessary, by adding an alkali metal iodide. (e.g. potassium iodide, sodium iodide) as a reaction promoter. The quantity ratio between the compound of general formula (7) and the compound of general formula (8) to be subjected to the above reaction is not critical but, generally, the latter is used in an amount of 1 mole or in excess, preferably 1 to 5 moles, per mole of the former.

The compounds of general formula (4) can be prepared also by the following process 2.

[Process 2]

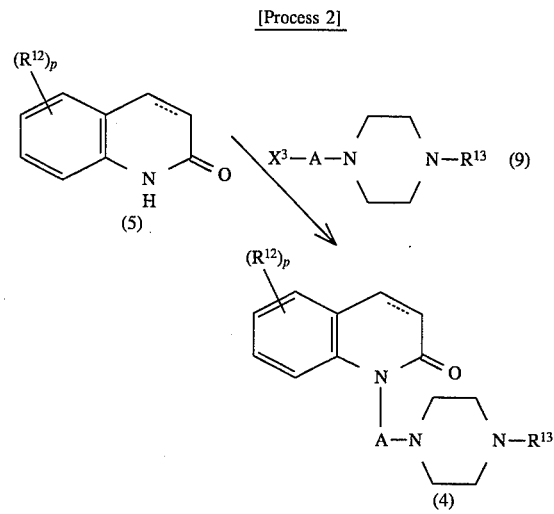

In the above reaction formula, $R^{12}$, $R^{13}$, A, p and the carbon-carbon bond between the positions of 3 and 4 of the carbostyril skeleton are as defined above and $X^3$ is a halogen atom.

In the above process 2, the reaction of the compound of general formula (5) with the compound of general formula (9) can be carried out in the same manner as mentioned above for the reaction of the compound of general formula (5) with the compound of general formula (6). The compound of general formula (9) can be readily prepared, for example, by reacting the compound of the foregoing general formula (8) with the compound of general formula (6). The reaction between the compound of general formula (6) and the compound of general formula (8) can be carried out in the same manner as mentioned above for the reaction between the compound of the foregoing general formula (7) and the compound of general formula (8).

Among the compounds of the invention which are represented by the above general formula (4), those compounds in which $R^{12}$ is a lower alkanoylamino group and those compounds in which $R^{13}$ is a phenyl group having at least one lower alkalnoylamino group as a substituent on the phenyl ring can be produced by lower alkanoylating the corresponding compounds in which $R^{12}$ is an amino group and those in which $R^{13}$ is a phenyl group having at least one amino group as a substituent on the phenyl ring, respectively.

The lower alkanoylation mentioned above is effected, for example, by reacting the starting compounds with a lower alkanoic acid anhydride without using any solvent or in an appropriate inert solvent, in the presence of a basic compound, or by reacting the starting compounds with a lower alkanoic acid anhydride or lower alkanoyl halide in an appropriate inert solvent. As the basic compound to be used, there may be mentioned organic bases such as pyridine, 4-dimethylaminopyridine and triethylamine and inorganic bases such as sodium carbonate and potassium carbonate. As the inert solvent, there may be mentioned, for example, acetic acid, pyridine, ethers such as dioxane, aromatic hydrocarbons such as benzene, and halogenated hydrocarbons such as dichloromethane and chloroform. The lower alkanoic acid anhydride or lower alkanoyl halide is used at least in an equimolar amount, generally in an amount ranging from equimolar to large excess. Said reaction is advantageously carried out at room temperature to about 150° C. and is generally complete in about 0.5 to about 5 hours.

Among the compounds of the invention which are represented by the above general formula (4), those compounds in which $R^{12}$ is an amino group and those compounds in which $R^{13}$ is a phenyl group having at least one amino group as a substituent on the phenyl ring can be produced by hydrolyzing the corresponding compounds in which $R^{12}$ is a lower alkanoylamino group and those in which $R^{13}$ is a phenyl group having at least one lower alkanoylamino group as a substituent on the phenyl ring, respectively.

The above hydrolysis is carried out in an appropriate inert solvent or without using any solvent, in the presence of an acid. The solvent may be any of those conventional ones which do not adversely affect the reaction, including, for example, water, halogenated hydrocarbons such as dichloroethane and chloroform, lower alcohols such as methanol, ethanol and isopropanol, ketones such as acetone and methyl ethyl ketone, ethers such as dioxane, tetrahydrofuran, ethylene glycol monomethyl ether and ethylene glycol dimethyl ether, fatty acids such as formic acid, and mixed solvents composed of these. As the acid, there may be mentioned, for example, inorganic acids such as hydrochloric acid, sulfuric acid and hydrobromic acid, and organic acids such as formic acid, trifluoroacetic acid, acetic acid and aromatic sulfonic acids. The amount of the acid is not critical but may be selected within a wide range. Generally, however, it is used preferably in an amount of about 1 to about 10 moles per mole of each starting compound. Generally, said reaction progresses smoothly at room temperature to about 200° C., preferably at room temperature to about 150° C. and is generally complete in about 0.5 to about 5 hours.

Among the compounds of the invention which are represented by the above general formula (4), those compounds in which $R^{13}$ is a phenyl group having at least one amino group as a substituent on the phenyl ring can be produced by reducing the corresponding compounds in which $R^{13}$ is a phenyl group having at least one nitro group as a substituent on the phenyl ring.

The above reduction reaction can be carried out, for example (1) by the catalytic reduction method using a catalyst in an appropriate solvent or (2) using a reducing agent such as a mixture of a metal or a metal salt with an acid or with an alkali metal hydroxide, a sulfide or an ammonium salt in an appropriate inert solvent.

In the case of catalytic reduction mentioned above under (1), the solvent to be used includes, among others, water, acetic acid, alcohols such as methanol, ethanol and isopropanol, hydrocarbons such as hexane and cyclohexane, ethers such as dioxane, tetrahydrofuran, diethyl ether and diethylene glycol dimethyl ether, esters such as ethyl acetate and methyl acetate, aprotic polar solvents such as N,N-dimethylformamide, and mixed solvents composed of these. The catalyst for catalytic reduction to be used is, for example, palladium, palladium black, palladium-carbon, platinum, platinum oxide, copper chromite, or Raney nickel. Preferably, said catalyst is used in an amount of about 0.02 to 1 part by weight per part of the starting compound. The reaction temperature is generally about −20° to about 150° C., preferably about 0° to about 100° C., and the hydrogen pressure is preferably about 1 to about 10 atmospheres. Said reaction is generally complete in about 0.5 to about 10 hours. An acid such as hydrochloric acid may be added to the reaction system for said reaction.

When the method mentioned above under (2) is used, the reducing agent to be used is, for example, a mixture of iron, zinc, tin or ferrous chloride and an inorganic acid such as hydrochloric acid or sulfuric acid or a mixture of iron, ferrous sulfate, zinc or tin and an alkali metal hydroxide such as sodium hydroxide, a sulfide such as ammonium sulfide, aqueous ammonia or an ammonium salt such as ammonium chloride. The inert solvent to be used is, for example, water, acetic acid, methanol, ethanol or dioxane. The conditions for the above reduction reaction may suitably be selected depending on the reducing agent employed. Thus, for instance, when the reducing agent comprises stannous chloride and hydrochloric acid, the reaction is recommendably carried out at about 0° C. to room temperature for about 0.5 to about 10 hours. The reducing agent is used at least in an equimolar amount relative to the starting compound, generally in an amount of 1 to 5 moles per mole of the starting compound.

Among the compounds of the invention which are represented by general formula (4), those compounds in which the carbon-carbon bond between the positions 3 and 4 of the carbostyril skeleton is a double bond can be produced by dehydrogenating the corresponding compounds in which said bond is a single bond, in the per se conventional manner. The other way around, those compounds in which the carbon-carbon bond between the positions 3 and 4 of the carbostyril skeleton is a single bond can be produced by subjecting the corresponding compounds in which said bond is a double bond to catalytic reduction in the per se conventional manner.

The compounds of general formula (1) to (4) and 3-methoxy-N-methylmorphinan which serve as active ingredients in accordance with the invention may readily form salts with pharmacologically acceptable conventional acids. As such acids, there may be mentioned inorganic acids such as sulfuric acid, nitric acid, hydrochloric acid and hydrobromic acid, and organic acids such as acetic acid, p-toluenesulfonic acid, ethanesulfonic acid, oxalic acid, maleic acid, fumaric acid, citric acid, succinic acid and benzoic acid. These salts can also be useless active ingredient compounds of the invention, just like the free compounds of general formula (1) to (4) and 3-methoxy-N-methylmorphinan. The compounds of general formula (1) to (4) and 3-methoxy-N-methylmorphinan include within the scope thereof all possible stereoisomers and optical isomers thereof. Such isomers can be used as active ingredient compounds as well.

The desired compounds obtained by the processes illustrated above by way of reaction formulas can be separated from the reaction systems by conventional means for separation and further purified. Useful as the means for separation and purification are, for example, distillation, recrystallization, column chromatography, ion exchange chromatography, gel chromatography, affinity chromatography, preparative thin layer chromatography, and solvent extraction.

The thus-obtained compounds, which have sigma receptor agonistic activity, are effective as disturbance-of-consciousness improving agents and can be used in the form of conventional pharmaceutical preparations. Such preparations are prepared using the conventional fillers, extenders, binding agents, moistening agents, disintegrating agents, surfactants, lubricants, and like diluents or excipients. These pharmaceutical preparations may have various dosage forms selected according to the purposes of therapy, and typical examples thereof are tablets, pills, powders, solutions, suspensions, emulsions, granules, granules, capsules, suppositories, and injections (solutions, suspensions, etc.). For the manufacture of tablets, a wide variety of carriers so far well known in this field can be used. Examples of useful carriers include vehicles or excipients such as lactose, sucrose, sodium chloride, glucose, urea, starch, calcium carbonate, kaolin, crystalline cellulose and silicic acid, binding agents such as water, ethanol, propanol, simple syrup, glucose solution, starch solution, gelatin solution, carboxymethylcellulose, shellac, methylcellulose, potassium phosphate and polyvinylpyrrolidone, disintegrating agents such as dry starch, sodium alginate, powdered agar, powdered laminaran, sodium hydrogen carbonate, calcium carbonate, polyoxyethylene sorbitan fatty acid esters, sodium lauryl sulfate, stearic acid monoglyceride, starch and lactose, disintegration inhibitors such as sucrose, stearin, cacao butter and hydrogenated oils, absorption promoters such as quaternary ammonium bases and sodium lauryl sulfate, wetting agents or humectants such as glycerol and starch, adsorbents such as starch, lactose, kaolin, bentonite and colloidal silica, and lubricants such as refined talc, stearic acid salts, powdered boric acid and polyethylene glycol. When necessary, the tablets may further be provided with a conventional coating, for example, sugar-coated tablets, gelatin-coated tablets, enteric-coated tablets, film-coated tablets, or double-coated or multilayer tablets. For the manufacture of pills, a wide variety of carriers well known in the art can be used. Examples are vehicles or excipients such as glucose, lactose, starch, cacao butter, hardened vegetable oils, kaolin and talc, binding agents such as powdered gum arabic, powdered tragacanth gum, gelatin and ethanol, and disintegrating agents such as laminaran and agar. For the manufacture of suppositories, a wide variety of carriers so far known can be used. As examples, there may be mentioned polyethylene glycol, cacao butter, higher alcohols, higher alcohol esters, gelatin and semisynthetic glycerides. Capsules are manufactured in the conventional manner, generally by filling each active ingredient compound in admixture with various carriers as mentioned above into hard gelatin capsules, soft capsules, etc. In preparing injections, the solutions, emulsions or suspensions are preferably sterilized and are preferably isotonic with blood and, for preparing such dosage forms, all the diluents in conventional use in this field can be employed. Thus, for example, water, ethyl alcohol, macrogol, propylene glycol, ethoxylated isostearyl alcohol, polyoxylated isostearyl alcohol and polyoxyethylene sorbitan fatty acid esters may be mentioned. In this case, the pharmaceutical preparations may contain sodium chloride, glucose or glycerol in an amount sufficient to give isotonic solutions. It is possible to add conventional solubilizing agents, buffers, soothing agents or local anesthetics, etc. Furthermore, when necessary, the pharmaceutical preparations may contain coloring matters, preservatives, perfumes, flavoring agents, sweetening agents and the like as well as other drugs.

The proportion of the active ingredient compound in these pharmaceutical preparations of this invention is not critical but may suitably be selected in a wide range. Generally, however, the proportion is within the range of about 1 to about 70% by weight, preferably about 5 to about 50% by weight.

The present invention also provides a therapeutic method of improving disturbance of consciousness, which comprises administrating a pharmacologically effective amount of a sigma receptor agonist compound.

The route of administration of these pharmaceutical preparations of this invention is not critical, either, but is selected according to the dosage form, the patient's age, sex and other factors and the severity of the disease to be treated. Thus, for instance, when they are provided in the form of tablets, pills, solutions, suspensions, emulsions, granules or capsules, the preparations are administered orally. Injectable solutions are administered intra-venously, either alone or in admixture with conventional fluids for parenteral infusion containing glucose, amino acids and so on. Where necessary, these solutions may also be administered as it is by the intramuscular, intradermal, subcutaneous or intraperitoneal route. Suppositories are administered rectally.

The dosage of these pharmaceutical preparations of the invention may be selected appropriately depending on the method of administration, the patient's age, sex and other factors, severity of the disease and other factors. Generally, however, the daily dose of the active ingredient compound is preferably within the range of about 0.0001 to about 50 mg per kilogram of body weight. It is desirable that the active ingredient compound be contained in each unit dosage form in an amount of about 0.001 to about 1,000 mg.

For illustrating the present invention in further detail, some dosage form examples are given below, which are followed by examples illustrating the production of the active ingredient compounds mentioned above and further by test examples using typical active ingredient compounds.

| Dosage Form Example 1 | |
|---|---|
| 2-Allyl-5,9-dimethoxy-2'-hydroxy-6,7-benzomorphan | 150 g |
| Avicel (trade name, product of Asahi Chemical Industry) | 40 g |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Ethanol | 40 g |

The active ingredient compound of this invention, Avicel, corn starch and magnesium stearate are combined and ground together and the resulting mixture is tableted using a sugar coat R10 mm punch. The tablets obtained are coated with a film coating composition composed of hydroxypropylmethylcellulose, polyethylene glycol 6000, castor oil and ethanol to give film-coated tablets.

| Dosage Form Example 2 | |
|---|---|
| 2-(3-Methyl-2-butenyl)-5,9-dimethoxy-2'-hydroxy-6,7-benzomorphan | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active ingredient compound of this invention, citric acid, lactose, dicalcium phosphate, Pluronic F-68 and sodium lauryl sulfate are admixed.

After size selection using a No. 60 screen, the mixture was granulated by the wet process using an alcoholic solution containing polyvinylpyrrolidone, Carbowax 1500 and Carbowax 6000. When necessary, alcohol is added to make the powder into a paste-like mass. Then, corn starch is added and the blending is continued until uniform granules are formed. The mixture is then passed through a No. 10 screen, placed in a tray and dried in an oven maintained at 100° C. for 12 to 14 hours. The dried granules are sieved through a No. 16 screen, dry sodium lauryl sulfate and dry magnesium stearate are added and, after blending, the mixture is compressed to a desired size and shape using a tableting machine.

The above cores are treated with a varnish and dusted with talc for preventing absorption of moisture and then provided with an undercoat layer. Varnish coating is repeated as many times as sufficient for internal use. The tablets are rendered completely round and smooth by application of a further undercoat layer and a smooth coating. Coloring coating is conducted until a desired coloring is obtained. After drying, the coated tablets are polished to give uniformly polished tablets.

| Dosage Form Example 3 | |
|---|---|
| 5-Chloro-1-{3-[4-(3-methoxyphenyl)-1-piperazinyl]propyl}-3,4-dihydrocarbostyril | 5 g |
| Polyethylene glycol (molecular weight: 4,000) | 0.3 g |
| Sodium chloride | 0.9 g |
| Polyoxyethylene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The above parabens, sodium metabisulfite and sodium chloride are dissolved in about half the above-specified volume of distilled water at 80° C. with stirring. The solution obtained is cooled to 40° C., the active ingredient compound of the invention is dissolved in said solution and then polyethylene glycol and polyoxyethylene sorbitan monooleate are dissolved therein. Then, the remaining portion of distilled water for injection is added to the solution to make the final volume and the resulting solution is sterilized by bacterial filtration using an appropriate filter paper to give an injectable solution.

| Dosage Form Example 4 | |
|---|---|
| N,N'-Di-(2-methylphenyl)guanidine | 150 g |
| Avicel (trade name, product of Asahi Chemical Industry) | 40 g |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Ethanol | 40 g |

The active ingredient compound of this invention, Avicel, corn starch and magnesium stearate are combined and ground together and the resulting mixture is tableted using a sugar coat R10 mm punch. The tablets obtained are coated with a film coating composition composed of hydroxypropylmethylcellulose, polyethylene glycol 6000, castor oil and ethanol to give film-coated tablets.

| Dosage Form Example 5 | |
| --- | --- |
| α-Cinnamyl-N-cyclopropylmethyl-α-ethyl-N-methylbenzylamine | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starcn | 30.0 g |
| Dry sodium stearate | 3.0 g |
| Dry magnesium stearate | 3.0 g |
| Ethanol | q.s. |

The active ingredient compound of this invention, citric acid, lactose, dicalcium phosphate, Pluronic F-68 and sodium lauryl sulfate are admixed.

After size selection using a No. 60 screen, the mixture was granulated by the wet process using an alcoholic solution containing polyvinylpyrrolidone, Carbowax 1500 and Carbowax 6000. When necessary, alcohol is added to make the powder into a paste-like mass. Then, corn starch is added and the blending is continued until uniform granules are formed. The mixture is then passed through a No. 10 screen, placed in a tray and dried in an oven maintained at 100° C. for 12 to 14 hours. The dried granules are sieved through a No. 16 screen, dry sodium lauryl sulfate and dry magnesium stearate are added and, after blending, the mixture is compressed to a desired size and shape using a tableting machine.

The above cores are treated with a varnish and dusted with talc for preventing absorption of moisture and then provided with an undercoat layer. Varnish coating is repeated as many times as sufficient for internal use. The tablets are rendered completely round and smooth by application of a further undercoat layer and a smooth coating. Coloring coating is conducted until a desired coloring is obtained. After drying, the coated tablets are polished to give uniformly polished tablets.

| Dosage Form Example 6 | |
| --- | --- |
| 5-Methoxy-1-{3-[4-(3-chlorophenyl)-1-piperazinyl]propyl}-3,4-dihydrocarbostyril | 150 g |
| Avicel (trade name, product of Asahi Chemical Industry) | 40 g |
| Corn starch | 30 g |
| Magnesium stearate | 2 g |
| Hydroxypropylmethylcellulose | 10 g |
| Polyethylene glycol 6000 | 3 g |
| Castor oil | 40 g |
| Ethanol | 40 g |

The active ingredient compound of this invention, Avicel, corn starch and magnesium stearate are combined and ground together and the resulting mixture is tableted using a sugar coat R10 mm punch. The tablets obtained are coated with a film coating composition composed of hydroxypropylmethylcellulose, polyethylene glycol 6000, castor oil and ethanol to give film-coated tablets.

| Dosage Form Example 7 | |
| --- | --- |
| 3-Methoxy-N-methylmorphinan | 150 g |
| Citric acid | 1.0 g |
| Lactose | 33.5 g |
| Dicalcium phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium stearate | 3.0 g |
| Dry magnesium stearate | 3.0 g |
| Ethanol | q.s. |

The active ingredient compound of this invention, citric acid, lactose, dicalcium phosphate, Pluronic F-68 and sodium lauryl sulfate are admixed.

After size selection using a No. 60 screen, the mixture was granulated by the wet process using an alcoholic solution containing polyvinylpyrrolidone, Carbowax 1500 and Carbowax 6000. When necessary, alcohol is added to make the powder into a paste-like mass. Then, corn starch is added and the blending is continued until uniform granules are formed. The mixture is then passed through a No. 10 screen, placed in a tray and dried in an oven maintained at 100° C. for 12 to 14 hours. The dried granules are sieved through a No. 16 screen, dry sodium lauryl sulfate and dry magnesium stearate are added and, after blending, the mixture is compressed to a desired size and shape using a tableting machine.

The above cores are treated with a varnish and dusted with talc for preventing absorption of moisture and then provided with an undercoat layer. Varnish coating is repeated as many times as sufficient for internal use. The tablets are rendered completely round and smooth by application of a further undercoat layer and a smooth coating. Coloring coating is conducted until a desired coloring is obtained. After drying, the coated tablets are polished to give uniformly polished tablets.

Reference Example 1

To a solution of 5-methoxy-3,4-dihydrocarbostyril (53.1 g, 0.3 mole) in 200 ml of dimethylformamide (DMF) was added portionwise 60% sodium hydride in oil (19.2 g, 0.4 mole) at room temperature, and the mixture was stirred for 30 minutes. To the thus-obtained solution of the sodium salt of 5-methoxy-3,4-dihydrocarbostyril in DMF was added 1-bromo-3-chloropropane (94 ml, 0.6 mole). The mixture was stirred at 80°–90° C. for 8 hours. The DMF was distilled off under reduced pressure, and the residue was extracted with chloroform. The extract was washed with water and dried (anhydrous magnesium sulfate), the chloroform was distilled off under reduced pressure, and the residue was recrystallized from ethanol to give 59 g of 1-(3-chloropropyl)-5-methoxy-3,4-dihydrocarbostyril as colorless needles.

Melting point 103°–105° C. $^1$H-NMR (CDCl$_3$, δ ppm): 2.09–2.28 (2H, m), 2.57–2.62 (2H, m), 2.90 (2H, t,J=7.5 Hz), 3.47 (1H, t, J=7.5 Hz), 3.62 (1H, t, J=7.5 Hz), 3.85 (3H, s), 4.05–4.12 (2H, m), 6.64 (1H, d, J=9 Hz), 6.72 (1H, d, J=9 Hz), 7.22 (1H, t, J=9 Hz)

Reference Example 2

In the same manner as in Reference Example 1, 60% sodium hydride in oil was added portionwise to a solution of 5-chloro-3,4-dihydrocarbostyril in DMF, the resultant mixture was stirred for 30 minutes, 1-bromo-3-chloropropane was then added, and the resultant mixture was further stirred at 80°–90° C. for 8 hours. The DMF was distilled off under reduced pressure, and the residue was extracted with chloroform. The extract was washed with water and dried (anhydrous magnesium sulfate), the chloroform was distilled off under reduced pressure, and the residue was purified by silica gel column chromatography to give 5-chloro-1-(3-chloropropyl)-3,4-dihydrocarbostyril as a pale yellow oil.

¹H-NMR (CDCl₃, δ ppm); 2.15–2.25 (2H, m), 2.65 (2H, t, J=7.5 Hz), 3.04 (2H, t, J=7.5 Hz), 3.48 (2H, t, J=7.5 Hz), 4.08 (2H, t, J=7.5 Hz), 6.99 (1H, d, J=9 Hz), 7.10 (1H, d, J=9 Hz), 7.20 (1H, t, J=9 Hz)

The procedure of Reference Example 1 was followed using appropriate starting materials to give the compounds of Reference Examples 3 to 10 as specified below.

Reference Example 3

1-(3-Chloropropyl)-5-ethoxy-3,4-dihydrocarbostyril, colorless oil

¹H-NMR (CDCl₃, δ ppm); 1.42 (3H, t, J=7.5 Hz), 2.08–2.28 (2H, m), 2.57–2.65 (2H, m), 2.91 (2H, t, J=7.5 Hz), 3.42 (1H, t, J=7.5 Hz), 3.62 (1H, t, J=7.5 Hz), 4.01–4.11 (4H, m), 6.62 (1H, d, J=9 Hz), 6.71 (1H, d, J=9 Hz), 7.20 (1H, t, J=9 Hz)

Reference Example 4

1-(3-Chloropropyl)-5-isopropoxy-3,4- dihydrocarbostyril, colorless oil

¹H-NMR (CDCl₃, δ ppm); 1.34 (6H, d, J=7.5 Hz), 2.01–2.29 (2H, m), 2.58–2.62 (2H, m), 2.89 (2H, t, J=7.5 Hz), 3.48 (1H, t, J=7.5 Hz), 3.63 (1H, t, J=7.5 Hz), 4.08 (2H, t, J=7.5 Hz), 4.50–4.60 (1H, m), 6.65 (1H, d, J=9 Hz), 6.69 (1H, d, J=9 Hz), 7.18 (1H, t, J=9 Hz)

Reference Example 5

1-(3-Chloropropyl)-5-methyl-3,4-dihydrocarbostyril, colorless oil

¹H-NMR (CDCl₃, δ ppm); 2.15–2.25 (2H, m), 2.30 (3H, s), 2.62 (2H, t, J=7.5 Hz), 2.84 (2H, t, J=7.5 Hz), 3.47 (2H, t, J=7.5 Hz), 4.08 (2H, t, J=7.5 Hz), 6.90 (1H, d, J=9 Hz), 6.94 (1H, d, J=9 Hz), 7.16 (1H, t, J=9 Hz)

Reference Example 6

1-(3-Chloropropyl)-5-methylthio-3,4- dihydrocarbostyril, yellow oil

¹H-NMR (CDCl₃, δ ppm); 2.09–2.25 (2H, m), 2.47 (3H, s), 2.59–2.70 (2H, m), 2.91–2.99 (2H, m), 3.36 (1H, t, J=7.5 Hz), 3.47 (1H, t, J=7.5 Hz), 4.08 (2H, t, J=7.5 Hz), 6.90 (1H, d, J=9 Hz), 6.94 (1H, d, J=9 Hz), 7.24 (1H, t, J=9 Hz)

Reference Example 7

1-(3-Chloropropyl)-8-methoxy-3,4-dihydrocarbostyril, colorless oil

¹H-NMR (CDCl₃, δ ppm); 2.10–2.30 (2H, m), 2.55–2.65 (2H, m), 2.70–2.80 (2H, m), 3.55 (2H, t, J=7.5 Hz), 3.85 (3H, t, J=7.5 Hz), 4.05 (2H, t, J=7.5 Hz), 6.80 (1H, d, J=9 Hz), 6.90 (1H, d, J=9 Hz), 7.05 (1H, t, J=9 Hz)

Reference Example 8

1-(3-Chloropropyl)-5,6-dichloro-3,4- dihydrocarbostyril, colorless oil

¹H-NMR (CDCl₃, δ ppm); 2.10–2.25 (2H, m), 2.64–2.70 (2H, m), 3.08–3.15 (2H, m), 3.47 (2H, t, J=7.5 Hz), 4.05 (2H, t, J=7.5 Hz), 6.95 (1H, d, J=9 Hz), 7.36 (1H, d, J=9 Hz)

Reference Example 9

5-Acetylamino-1-(3-chloropropyl)-3,4- dihydrocarbostyril, colorless oil

¹H-NMR (CDCl₃, δ ppm); 2.10–2.25 (2H, m), 2.15 (3H, s), 2.64–2.70 (2H, m), 3.08–3.15 (2H, m), 3.48 (2H, t, J=7.5 Hz), 4.05 (2H, t, J=7.5 Hz), 6.62 (1H, d, J=7.5 Hz), 6.75 (1H, d, J=9 Hz), 7.25 (1H, t, J=9 Hz)

Reference Example 10

1-(3-Chloropropyl)-5-methoxycarbostyril, colorless oil

¹H-NMR)CDCl₃, δ ppm); 2.15–2.38 (2H, m), 3.55 (2H, t, J=7.5 Hz), 3.96 (3H, s), 4.42 (2H, t, J=7.5 Hz), 6.62 (1H, d, J=10 Hz), 6.65 (1H, d, J=9 Hz), 7.05 (1H, t, J=9 Hz), 7.50 (1H, t, J=9 Hz), 8.15 (1H, d, J=10 Hz)

EXAMPLE 1

A solution composed of 1-(3-chloropropyl)-5-methoxy-3,4-dihydrocarbostyril (39.1 g, 0.15 mole), sodium iodide (33.5 g, 0.23 mole) and acetonitrile (200 ml) was heated under reflux for 1 hour and then cooled to room temperature. To this solution was further added 1-(3-chlorophenyl)-piperazine (39.3 g, 0.2 mole) and sodium carbonate (21 g, 0,2 mole). The mixture was further stirred for 4 hours and then filtered while it was hot. The filtrate was concentrated under reduced pressure. The residue was purified by silica gel column chromatography, made acidic with hydrochloric acid and then recrystallized from ethanol to give 31.2 g of 1-{3-[4-(3-chlorophenyl)-1-piperazinyl]propyl}-5-methoxy-3,4-dihydrocarbostyril hydrochloride as colorless flakes.

Melting point 239°–242° C. (decomposition).

EXAMPLES 2 TO 56

The procedure of Example 1 was followed using appropriate starting materials to give the compounds listed below in Table 1. In Table 1, the solvent means a solvent for recrystallization.

TABLE 1

| Example | Structure | Crystal Form (solvent) | mp (°C.) |
|---|---|---|---|
| 2 | 5-Cl-3,4-dihydroquinolin-2(1H)-one, N-substituted with -(CH₂)₃-piperazine-(3-methoxyphenyl), 2HCl | colorless needles (methanol) | 212–213 (dec.) |
| 3 | 5-OCH₃-3,4-dihydroquinolin-2(1H)-one, N-substituted with -(CH₂)₃-piperazine-(3-bromophenyl), HCl | colorless needles (ethanol) | 228–231 (dec.) |
| 4 | 5-OCH₃-3,4-dihydroquinolin-2(1H)-one, N-substituted with -(CH₂)₃-piperazine-(3-trifluoromethylphenyl), HCl | colorless needles (ethanol) | 207–208 |
| 5 | 5-OCH₃-3,4-dihydroquinolin-2(1H)-one, N-substituted with -(CH₂)₃-piperazine-(3,5-dichlorophenyl), HCl | white powder (ethanol) | 226–228 (dec.) |
| 6 | 5-OCH₂CH₃-3,4-dihydroquinolin-2(1H)-one, N-substituted with -(CH₂)₃-piperazine-(3-chlorophenyl), HCl | white powder (ethanol) | 226–228 (dec.) |
| 7 | 5-OCH(CH₃)₂-3,4-dihydroquinolin-2(1H)-one, N-substituted with -(CH₂)₃-piperazine-(3-chlorophenyl), HCl | colorless flakes (ethanol) | 218–229 (dec.) |

TABLE 1-continued

| Example | Structure | Crystal Form (solvent) | mp (°C.) |
|---|---|---|---|
| 8 | 5-CH₃ carbostyril, N-(CH₂)₃-piperazine-(3-Cl-phenyl)·HCl | colorless needles (ethanol) | 196–198 |
| 9 | 5-OCH₃ carbostyril, N-(CH₂)₃-piperazine-(3-CH₃-phenyl)·HCl | colorless needles (ethanol) | 220–228 (dec.) |
| 10 | 5-OCH₃ carbostyril, N-(CH₂)₃-piperazine-(2-OCH₂CH₃-phenyl)·HCl | colorless needles (ethanol) | 168–173 (dec.) |
| 11 | 5-SCH₃ carbostyril, N-(CH₂)₃-piperazine-(3-Cl-phenyl)·HCl | colorless needles (ethanol) | 221–224 (dec.) |
| 12 | 5-OCH₃ carbostyril, N-(CH₂)₃-piperazine-(2-Cl-phenyl)·HCl | colorless needles (ethanol) | 214–215 (dec.) |
| 13 | 5-OCH₃ carbostyril, N-(CH₂)₃-piperazine-(4-Cl-phenyl) | colorless needles (ethanol) | 124–125 |

TABLE 1-continued

| Example | Structure | Crystal Form (solvent) | mp (°C.) |
|---|---|---|---|
| 14 | 5-OCH₃-3,4-dihydroquinolin-2(1H)-one, N-substituted with -(CH₂)₃-piperazine-(3-fluorophenyl), HCl | colorless needles (ethanol) | 236–240 (dec.) |
| 15 | 5-OCH₃-3,4-dihydroquinolin-2(1H)-one, N-substituted with -(CH₂)₂-piperazine-(3-chlorophenyl) | colorless needles (ethanol) | 132–132.5 |
| 16 | 5-OCH₃-3,4-dihydroquinolin-2(1H)-one, N-substituted with -(CH₂)₄-piperazine-(3-chlorophenyl), HCl | colorless needles (ethanol) | 128–129 (dec.) |
| 17 | 5-OCH₃-3,4-dihydroquinolin-2(1H)-one, N-substituted with -(CH₂)₃-piperazine-(4-methylphenyl), HCl | colorless needles (ethanol) | 226–229 (dec.) |
| 18 | 5-OCH₃-3,4-dihydroquinolin-2(1H)-one, N-substituted with -(CH₂)₃-piperazine-(3-methoxyphenyl), HCl | colorless needles (ethanol) | 176–177 |
| 19 | 5-OCH₃-3,4-dihydroquinolin-2(1H)-one, N-substituted with -(CH₂)₃-piperazine-(2,5-dimethylphenyl), HCl | colorless needles (ethanol) | 223–226 (dec.) |

TABLE 1-continued

| Example | Structure | Crystal Form (solvent) | mp (°C.) |
|---|---|---|---|
| 20 | 5-OCH₃ carbostyril, N-(CH₂)₃-piperazine-(2,3-dimethylphenyl) · HCl | colorless needles (ethanol) | 228–230 (dec.) |
| 21 | 5-OCH₃ carbostyril, N-(CH₂)₃-piperazine-(2-methyl-3-chlorophenyl) · 2HCl | colorless needles (ethanol) | 232–234 (dec.) |
| 22 | 5-OCH₃ carbostyril, N-(CH₂)₃-piperazine-(3,4-dimethylphenyl) · HCl | colorless needles (ethanol) | 212–216 |
| 23 | 5-Cl carbostyril, N-(CH₂)₃-piperazine-(3-chlorophenyl) · 2HCl | colorless needles (ethanol) | 217–218 (dec.) |
| 24 | 5-OH carbostyril, N-(CH₂)₃-piperazine-(2-methyl-3-chlorophenyl) | colorless prisms (ethanol) | 185.5–186.5 |
| 25 | 5-CH₃ carbostyril, N-(CH₂)₃-piperazine-(3-methoxyphenyl) · HCl | colorless needles (ethanol) | 145–146 |

TABLE 1-continued

| Example | Structure | Crystal Form (solvent) | mp (°C.) |
|---|---|---|---|
| 26 | 6-CH₃O-quinolin-2(1H)-one, 1-[3-[4-(3-chlorophenyl)piperazin-1-yl]propyl]-3,4-dihydro- | white powder (ethanol) | 159–161 |
| 27 | 7-CH₃O-quinolin-2(1H)-one, 1-[3-[4-(3-chlorophenyl)piperazin-1-yl]propyl]-3,4-dihydro-, HCl | colorless needles (ethanol) | 224–229 (dec.) |
| 28 | 7-CH₃-quinolin-2(1H)-one, 1-[3-[4-(3-chlorophenyl)piperazin-1-yl]propyl]-3,4-dihydro-, HCl | white powder (ethanol) | 136–137 |
| 29 | 5-OCH₂CH=CH₂-quinolin-2(1H)-one, 1-[3-[4-(3-chlorophenyl)piperazin-1-yl]propyl]-3,4-dihydro-, HCl | colorless needles (ethanol) | 180–185 |
| 30 | 7-Cl-quinolin-2(1H)-one, 1-[3-[4-(3-chlorophenyl)piperazin-1-yl]propyl]-3,4-dihydro-, HCl | colorless needles (ethanol) | 172–173 |
| 31 | 7-Cl-quinolin-2(1H)-one, 1-[3-[4-(3-methoxyphenyl)piperazin-1-yl]propyl]-3,4-dihydro-, HCl | colorless needles (ethanol) | 185–187 |
| 32 | 5-OH-quinolin-2(1H)-one, 1-[3-[4-(3-chlorophenyl)piperazin-1-yl]propyl]-3,4-dihydro- | colorless prisms (ethanol) | 200–201.5 (dec.) |

TABLE 1-continued

| Example | Structure | Crystal Form (solvent) | mp (°C.) |
|---|---|---|---|
| 33 | (structure: 5-chloro-3,4-dihydroquinolin-2(1H)-one with N-propyl-piperazinyl-(3-nitrophenyl), HCl) | yellow needles (ethanol) | 204–211 (dec.) |
| 34 | (structure: 5-chloro-3,4-dihydroquinolin-2(1H)-one with N-propyl-piperazinyl-(3-aminophenyl)) | colorless needles (ethanol) | 161–163 |
| 35 | (structure: 5-chloro-3,4-dihydroquinolin-2(1H)-one with N-propyl-piperazinyl-(3-acetamidophenyl), HCl) | colorless needles (ethanol) | 177–178 |
| 36 | (structure: 5-chloro-3,4-dihydroquinolin-2(1H)-one with N-propyl-piperazinyl-(3-hydroxyphenyl)) | colorless granulars (dimethylformamide-methanol) | 236–239 |
| 37 | (structure: 5-chloro-3,4-dihydroquinolin-2(1H)-one with N-propyl-piperazinyl-(3-propoxyphenyl), HCl) | colorless granulars (ethanol) | 186–188 |
| 38 | (structure: 5-chloro-3,4-dihydroquinolin-2(1H)-one with N-propyl-piperazinyl-(3-benzyloxyphenyl), HCl) | colorless granulars (ethanol) | 181–183 |

TABLE 1-continued

| Example | Structure | Crystal Form (solvent) | mp (°C.) |
|---------|-----------|------------------------|----------|
| 39 | OCH₃ quinolinone · HCl with piperazine-(3-Cl-phenyl) | colorless needles (ethanol) | 232–236 (dec.) |
| 40 | OCH₃ quinolinone · HCl with piperazine-(3-Br-phenyl) | colorless needles (ethanol) | 222–232 (dec.) |
| 41 | OCH₃ quinolinone · HCl with piperazine-(3-CF₃-phenyl) | colorless granulars (ethanol) | 221–228 (dec.) |
| 42 | 8-CH₃O-3,4-dihydroquinolinone · HCl with piperazine-(3-Cl-phenyl) | white powder (ethanol) | 196–201 |
| 43 | 5-NHCOCH₃-3,4-dihydroquinolinone · HCl with piperazine-(3-Cl-phenyl) | colorless granulars (ethanol) | 177–183 (dec.) |
| 44 | 5-NH₂-3,4-dihydroquinolinone · 2HCl with piperazine-(3-Cl-phenyl) | white powder (ethanol) | 218–240 (dec.) |

TABLE 1-continued

| Example | Structure | Crystal Form (solvent) | mp (°C.) |
|---|---|---|---|
| 45 | (5,6-dichloro-3,4-dihydroquinolin-2(1H)-one, N-substituted with -(CH₂)₃-piperazine-(3-methoxyphenyl)·HCl) | colorless flakes (ethanol) | 212–216 |
| 46 | (8-methoxy-3,4-dihydroquinolin-2(1H)-one, N-substituted with -(CH₂)₃-piperazine-(2,5-dichlorophenyl)·HCl) | white powder (ethanol) | 215–221 (dec.) |
| 47 | (5-methoxy-3,4-dihydroquinolin-2(1H)-one, N-substituted with -(CH₂)₃-piperazine-(3,4-dichlorophenyl)·HCl) | white powder (ethanol) | 228–234 |
| 48 | (5-methoxy-3,4-dihydroquinolin-2(1H)-one, N-substituted with -(CH₂)₃-piperazine-(3-nitrophenyl)·2HCl) | colorless flakes (ethanol) | 221–222 (dec.) |
| 49 | (5-methoxy-3,4-dihydroquinolin-2(1H)-one, N-substituted with -(CH₂)₃-piperazine-(3-aminophenyl)) | brown granulars (ethanol) | 132–133 |
| 50 | (5-methoxy-3,4-dihydroquinolin-2(1H)-one, N-substituted with -(CH₂)₃-piperazine-(3-acetamidophenyl)·2HCl) | pale yellow powder (ethanol) | 198–201 |

TABLE 1-continued

| Example | Structure | Crystal Form (solvent) | mp (°C.) |
|---|---|---|---|
| 51 | 5-OCH₃ quinolin-2(1H)-one with N-(CH₂)₃-piperazine-(3-hydroxyphenyl) · HCl | white powder (ethanol) | 205–208 (dec.) |
| 52 | 5-OCH₃ quinolin-2(1H)-one with N-(CH₂)₃-piperazine-(3-O-(CH₂)₃CH₃-phenyl) · 2HCl | white powder (ethanol) | 176–179 |
| 53 | 5-OCH₃ quinolin-2(1H)-one with N-(CH₂)₃-piperazine-(3-OCH(CH₃)₂-phenyl) · 2HCl | white powder (ethanol) | 170–173 |
| 54 | 5-OCH₃ quinolin-2(1H)-one with N-(CH₂)₃-piperazine-(3-O-CH₂-phenyl-phenyl) · HCl | white powder (ethanol) | 184–186 (dec.) |
| 55 | 5-OCH₃ quinolin-2(1H)-one with N-(CH₂)₃-piperazine-(3-CN-phenyl) · HCl | colorless flakes (ethanol) | 235–236 |
| 56 | 5-OCH₃ quinolin-2(1H)-one with N-(CH₂)₃-piperazine-phenyl · HCl | colorless flakes (ethanol) | 240–243 (dec.) |

EXAMPLE 57

5-Chloro-1-{3-[4-(3-nitrophenyl)-1-piperazinyl]propyl}-3,4-dihydrocarbostyril (3 g) was dissolved in 100 ml of ethanol, 2 ml of concentrated hydrochloric acid was added, and catalytic reduction was carried out at 3 atmospheres in the presence of 1.5 g of 5% palladium-carbon. The catalyst was then filtered off, the filtrate was concentrated under reduced pressure, and the residue was recrystallized from ethanol to give 2.5 g of 1-{3-[4-(3-aminophenyl)-1-piperazinyl]propyl}-5-chloro-3,4-dihydrocarbostyril as colorless needles.

Melting point 161°–163° C.

EXAMPLE 58

1-{3-[4-(3-aminophenyl)-1-piperazinyl]propyl}-5-chloro-3,4-dihydrocarbostyril (1 g) was dissolved in 10 ml of chloroform, 5 ml of acetic anhydride and 0.1 g of 4-dimethylaminopyridine were added, and the mixture was heated under reflux for 30 minutes. The reaction mixture was concentrated under reduced pressure, and the residue was purified by silica gel column chromatography and then converted to the hydrochloride form, which was recrystallized from ethanol to give 900 mg of 1-{3-[4-(3-acetylaminophenyl)-1-piperazinyl]propyl}-5-chloro-3,4-dihydrocarbostyril hydrochloride as colorless needles.

Melting point 177°–178° C.

EXAMPLE 59

5-Acetylamino-1-{3-[4-(3-chlorophenyl)-1-piperazinyl]propyl}-3,4-dihydrocarbostyril (800 mg) was dissolved in 20 ml of 6 N hydrochloric acid, and the mixture was heated under reflux for 1 hour. The reaction mixture was concentrated under reduced pressure and the residue was recrystallized from ethanol to give 480 mg of 5-amino-1-{3-[4-(3-chlorophenyl)-1-piperazinyl]propyl}-3,4-dihydrocarbostyril dihydrochloride as a white powder.

Melting point 218°–240° C. (decomposition).

EXAMPLE 60

The compound of Example 49 was produced by following the procedure of Example 57 using the corresponding starting material.

EXAMPLE 61

The compounds of Example 43 and Example 50 were produced by following the procedure of Example 58 using the corresponding starting materials.

EXAMPLE 62

The compounds of Example 44 and Example 49 were produced by following the procedure of Example 59 using the corresponding starting materials.

Test compounds 1–15

1. 1-{3-[4-(3-Chlorophenyl)-1-piperazinyl]propyl}-5-methoxy-3,4-dihydrocarbostyril hydrochloride
2. 1-{3-[4-(3-Methoxyphenyl)-1-piperazinyl]propyl}-5-chloro-3,4-dihydrocarbostyril dihydrochloride
3. 1-{3-[4-(3-Trifluoromethylphenyl)-1-piperazinyl]propyl}-5-methoxy-3,4-dihydrocarbostyril hydrochloride
4. 1-{3-[4-(Chlorophenyl)-1-piperazinyl]propyl}-5-methoxycarbostyril hydrochloride
5. 1-{3-[4-(3-Trifluoromethylphenyl)-1-piperazinyl]propyl}-5-methoxycarbostyril hydrochloride
6. 1-{3-[4-(3-Nitrophenyl)-1-piperazinyl]propyl}-5-methoxy- 3,4-dihydrocarbostyril dihydrochloride
7. 1-{3-[4-(3-Aminophenyl)-1-piperazinyl]propyl}-5-methoxy-3,4-dihydrocarbostyril
8. 1-{3-[4-(3-Isopropoxyphenyl)-1-piperazinyl]propyl}-5-methoxy-3,4-dihydrocarbostyril dihydrochloride
9. 1-[3-(4-phenyl-1-piperazinyl)propyl]-5-methoxy-3,4-dihydrocarbostyril hydrochloride
10. 2-Allyl-5,9-dimethyl-2'-hydroxy-6,7-benzomorphan,
11. N,N'-Di-(2-methylphenyl)guanidine
12. α-Cinnamyl-N-cyclopropylmethyl-α-ethyl-N-methylbenzylamine
13. 2-(3-Methyl-2-butenyl)-5,9-dimethyl-2'-hydroxy-6,7-benzomorphan
14. 4-[4-(5-Fluoro-2-pyrimidinyl)-1-piperazinyl]-1-(4-fluorophenyl)butanol
15. Cis-9-[3-(3,5-dimethylpiperazinyl)propyl]carbazole

Pharmacological test 1

Evaluation of disturbance-of-consciousness improving effect in a mouse model of coma following head injury The test was conducted according to the method described in the Journal of Japan Accident Medical Association, 25, 202 (1977) and Igaku no Ayumi, 102, 867–869 (1977). Thus, 4- to 5-week-old male mice (weighing 20–29 g) were fasted for 18–20 hours. Then, the head of each mouse was fixed on a polystyrene foam pillow and a shock was given to the parietal region by dropping a cylindrical acrylic resin rod through a clear plastic tube. Observation of impaired consciousness was made in regard to the following two terms: the time from the onset of coma following the shock to recovery of righting reflex (RR time) and the time to recovery of spontaneous mobility (SM time). Each test compound, either suspended or dissolved in a 5% solution of gum arabic solution in physiological saline, was administered orally one hour before anesthesia loading. Control mice received 5% gum arabic in saline. The disturbance-of-consciousness improving effect of the test compound was expressed in the ratio of the RR or SM time for the mice treated with the test compound to the RR or SM time for the control mice (% of control). The results are shown in Table 2.

TABLE 2

| Test compound | Route of administration and dose (mg/kg) | | RR time (% of control) | SM time (% of control) |
| --- | --- | --- | --- | --- |
| 1 | Oral | 30 | 20 | 20 |
| 2 | Oral | 30 | 28 | 28 |
| 3 | Oral | 30 | 36 | 48 |
| 5 | Oral | 30 | 51 | 58 |
| 6 | Oral | 30 | 52 | 52 |
| 10 | Subcutaneous | 3 | 27 | 35 |
| 11 | Intraperitoneal | 10 | 22 | 21 |
| 12 | Intraperitoneal | 10 | 40 | 48 |
| 13 | Subcutaneous | 1 | 42 | 50 |
| 14 | Oral | 3 | 128 | 140 |
|  | Subcutaneous | 30 | 187 | 193 |
| 15 | Oral | 30 | 88 | 88 |
|  | Oral | 300 | 422 | 290 |

In Table 2, as an indicator of recovery from the coma caused by head injury, the RR or SM time for mice treated with each test compound is shown in percentage with the RR or SM time for control mice being taken as 100%. The test compounds 1–3, 5, 6 and 10–12 of the present invention clearly shortened both the RR time and SM time in this model, indicating that the compounds accelerate recovery from the coma caused by head injury and have an ameliorative effect on impaired consciousness. On the other hand, the test compounds 14 and 15, which are sigma receptor antagonists, delay the mice's recovery from the coma.

Pharmacological Test 2

Binding affinity for the sigma receptor

A membrane fraction was prepared and a [$^3$H]-1,3-di[2-tolyl]guanidine (DTG) binding test was performed, both by the method of Wettstein et al. [Wettstein, J. F., Romman, F. J., Rocher, M. N. and Junien, J. L., Psychopharmacology, 104, 157–163 (1991)]. Thus, a Wistar strain male rat was decapitated and the whole brain was excised and homogenized in 30 volumes of ice-cooled 50 mM Tris hydrochloride buffer (pH 7.4). The homogenate was then centrifuged at 4° C. and 50,000 g for 15 minutes. The sediment obtained was suspended in one volume of the same buffer as mentioned above and, after 45 minutes of incubation at 37° C., the suspension was centrifuged again. The sediment obtained was suspended in one volume of the same buffer and the suspension was stored frozen at –80° C. until use.

The binding experiment was performed as follows. The frozen tissue preparation was thawed and centrifuged at 4° C. and 50,000 g for 15 minutes and the sediment obtained was suspended in 10 volumes of 5 mM Tris hydrochloride buffer (pH 7.4). The suspension was used as the membrane preparation. In test tubes were placed varying dilutions of the test compound (50 μl), [$^3$H]-DTG (50 μl, final concentration 3 nM) and the membrane preparation (150 μl) (total volume 250 μl per tube). The reaction began on addition of the membrane preparation. The tubes were incubated at 25° C. for 60 minutes and using a cell harvester (Brandel), the reaction was stopped by suction filtration through a Whatman GF/B filter saturated in advance with 0.5% polyethylenimine and the filter was immediately washed with three 3-ml portions of ice-cooled 5 mM Tris hydrochloride, buffer.

The filter was transferred to a vial and after addition of 5 ml of a liquid scintillation cocktail (Aquasol 2), the vial was allowed to stand in the dark for a predetermined time. The radioactivity was then measured using a scintillation counter. The amount of specific binding was determined by subtracting the binding amount in the presence of 10 μM haloperidol from the total binding amount. The IC$_{50}$ values were calculated by computer analysis using the nonlinear least squares method.

The results are shown in Table 3.

TABLE 3

| Test compound | Inhibitory activity IC$_{50}$ (μM ± SED) |
|---|---|
| 1 | 0.34 ± 0.11 |
| 2 | 0.13 ± 0.016 |
| 3 | 0.49 ± 0.032 |
| 4 | 0.98 ± 0.13 |
| 5 | 0.82 ± 0.11 |
| 6 | 0.87 ± 0.14 |
| 7 | 1.21 ± 0.14 |

TABLE 3-continued

| Test compound | Inhibitory activity IC$_{50}$ (μM ± SED) |
|---|---|
| 8 | 0.49 ± 0.048 |
| 9 | 0.71 ± 0.066 |
| 10 | 0.05 ± 0.017 |
| 11 | 0.4 ± 0.04 |
| 13 | 0.17 ± 0.008 |

Pharmacological study 3

Antagonistic experiment with sigma receptor antagonists

Whether the improving effect of sigma receptor agonists on impaired consciousness is due to their effect on specific receptors was investigated using test compounds 14 and 15 which are sigma receptor antagonists. Table 4 shows whether pretreatment with these antagonists in the dose of 1–3 mg (test compound 14) or 10–30 mg (test compound 15) per kg body weight at which they exerted no effect on impaired consciousness antagonized the disturbance-of-consciousness improving effect of test compounds 10, 11 and 12 which are sigma receptor agonists. As shown in Table 4, the disturbance-of-consciousness improving effect of test compounds 10 and 12 was inhibited by the sigma receptor antagonist test compound 14 administered in the dose of 1–3 mg per kg body weight. Similarly, the disturbance-of-consciousness improving effect of test compounds 10 and 12 was inhibited by 30 mg of another sigma receptor antagonist test compound 15. The fact that the disturbance-of-consciousness improving effect of these sigma receptor agonists was inhibited by two structurally different sigma receptor antagonists indicates that the disturbance-of-consciousness improving effect of these sigma receptor agonists is due, at least in part, to their effect on sigma receptors.

TABLE 4

| Test compound | Dose (mg/kg) | RR time (% control) | SM time (% control) |
|---|---|---|---|
| Control | 0 | 100 | 100 |
| 1 | 10 | 32 | 38 |
| 1 + 14 | 10 + 1 | 84 | 123 |
| 1 + 14 | 10 + 3 | 80 | 113 |
| Control | 0 | 100 | 100 |
| 10 | 3 | 32 | 34 |
| 10 + 14 | 3 + 1 | 81 | 83 |
| 10 + 14 | 3 + 3 | 91 | 94 |
| Control | 0 | 100 | 100 |
| 10 | 3 | 27 | 35 |
| 10 + 15 | 3 + 10 | 50 | 50 |
| 10 + 15 | 3 + 30 | 88 | 89 |
| Control | 0 | 100 | 100 |
| 11 | 10 | 22 | 21 |
| 11 + 15 | 10 + 10 | 35 | 42 |
| 11 + 15 | 10 + 30 | 50 | 88 |
| Control | 0 | 100 | 100 |
| 12 | 10 | 40 | 48 |
| 12 + 14 | 10 + 1 | 66 | 83 |
| 12 + 14 | 10 + 3 | 94 | 112 |

What is claimed is:

1. A therapeutic method of improving disturbance of consciousness, which comprises administering a pharmacologically effective amount of a sigma receptor agonist compound wherein said amount is from about 0.0001 to 50 mg/kg of body weight per day.

2. The therapeutic method according to claim 1 wherein the disturbance of consciousness is a primary lesion caused by cerebral hemorrhage, cerebral thrombosis, cerebral infarction subarachnoid hemorrhage, head injury, brain tumor, cerebral edema, encephalitis, meningitis, demyelinating disease, epilepsy or brain surgery.

3. The therapeutic method according to claim 1 wherein the disturbance of consciousness is a secondary lesion caused by hypoglycemia, diabetic ketoacidosis, lacticemic acidosis, hyponatremia, hypernatremia, hypercalcemia, hypocalcemia, liver damage, hepatic coma, kidney disorder, hypoxia, hypertensive encephalopathy, severe anemia, circulatory failure, cardiac arrest, bypass surgery, alcoholism, poisoning by hypnotics, psychotropic drugs, potassium cyanide or other drugs, carbon monoxide poisoning, abnormal body temperature (hypothermia, hyperthermia) or shock.

4. The therapeutic method according to claim 1 wherein the sigma receptor agonist compound is a benzomorphan derivative represented by the formula:

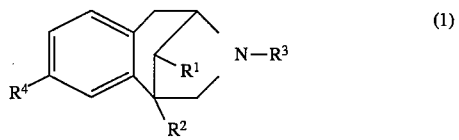

wherein $R^1$ and $R^2$ each represent hydrogen or lower alkyl; $R^3$ represents hydrogen, lower alkyl, lower alkenyl or cycloalkylmethyl; and $R^4$ represents hydroxy or lower alkoxy.

5. The therapeutic method according to claim 1 wherein the sigma receptor agonist compound is a guanidine derivative represented by the formula:

wherein $R^5$ and $R^6$ each represent $C_4$ or higher alkyl, $C_{3-12}$ cycloalkyl, or $C_6$ or higher carbocyclic aryl.

6. The therapeutic method according to claim 1 wherein the sigma receptor agonist compound is an N-cycloalkyl-benzylamine derivative represented by the formula:

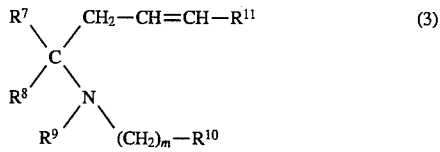

wherein $R^7$ represents phenyl which may be substituted by 1 to 3 members selected from halogen, lower alkyl, halo(lower) alkyl and lower alkoxy on the phenyl ring; $R^8$ represents lower alkyl; $R^9$ represents hydrogen or lower alkyl; $R^{10}$ represents cycloalkyl which may be substituted by lower alkyl or phenyl on the cycloalkyl ring; $R^{11}$ represents phenyl which may be substituted by 1 to 3 members selected from halogen and lower alkoxy on the phenyl ring; and m is equal to 1 or 2.

7. The therapeutic method according to claim 1, wherein the sigma receptor agonist compound is a carbostyril derivative represented by the following formula or a salt thereof:

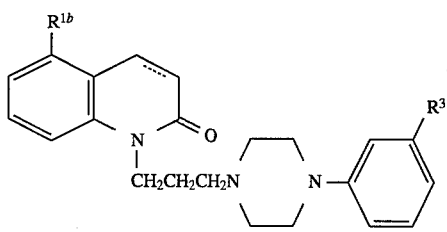

wherein $R^{1b}$ is selected from the group consisting of a methoxy, ethoxy, methyl and chloro group, $R^3$ is selected from the group consisting of a methoxy, chloro, bromo, nitro, hydroxyl and trifluoromethyl group; the carbon-carbon bond between the positions 3 and 4 of the carbostyril skeleton is a single bond or a double bond.

8. The therapeutic method according to claim 1 wherein the sigma receptor agonist compound is at least one compound selected from the group consisting of 2-allyl-5,9-dimethyl-2'-hydroxy-6,7-benzomorphan, 2-(3-methyl-2-butenyl)-5,9-dimethyl-2'-hydroxy-6,7-benzomorphan, 2-cyclopropylmethyl-5,9-dimethyl-2'-hydroxybenzomorphan, 2-methyl-5,9-dimethyl-2'-hydroxybenzomorphan, N,N'-di-(2-methylphenyl)guanidine, α-cinnamyl-N-cyclopropylmethyl-α-ethyl-N-methylbenzylamine, 5-methoxy-1-{3-[4-(3-chlorophenyl)-1-piperazinyl]propyl}-3,4-dihydrocarbostyril, 5-methoxy-1-{3-[4-(3-bromophenyl)-1-piperazinyl]propyl}-3,4-dihydrocarbostyril, 5-methoxy-1-{3-[4-(3-nitrophenyl)-1-piperazinyl]propyl}-3,4-dihydrocarbostyril, 5-ethoxy-1-{3-[4-(3-chlorophenyl)-1-piperazinyl]propyl}-3,4-dihydrocarbostyril, 5-chloro-1-{3-[4-(3-methoxyphenyl)-1-piperazinyl]propyl}-3,4-dihydrocarbostyril and 3-methoxy-N-methylmorphinan.

9. The therapeutic method according to claim 2 wherein the sigma receptor agonist compound is the benzomorphan derivative represented by formula (1):

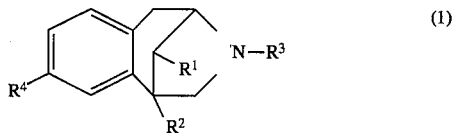

wherein $R^1$ and $R^2$ each represent hydrogen or lower alkyl; $R^3$ represents hydrogen, lower alkyl, lower alkenyl or cycloalkylmethyl; and $R^4$ represents hydroxy or lower alkoxy.

10. The therapeutic method according to claim 3 wherein the sigma receptor agonist compound is the benzomorphan derivative represented by formula (1):

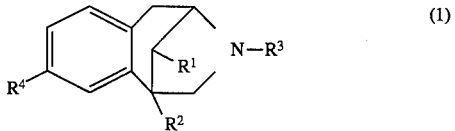

wherein $R^1$ and $R^2$ each represent hydrogen or lower alkyl; $R^3$ represents hydrogen, lower alkyl, lower alkenyl or cycloalkylmethyl; and $R^4$ represents hydroxy or lower alkoxy.

11. The therapeutic method according to claim 2 wherein the sigma receptor agonist compound is the guanidine derivative represented by formula (2):

wherein $R^5$ and $R^6$ each represent $C_4$ or higher alkyl; $C_{3-12}$ cycloalkyl, or $C_6$ or higher carbocyclic aryl.

12. The therapeutic method according to claim 3 wherein the sigma receptor agonist compound is the guanidine derivative represented by formula (2):

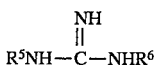

wherein $R^5$ and $R^6$ each represent $C_4$ or higher alkyl; $C_{3-12}$ cycloalkyl, or $C_6$ or higher carbocyclic aryl.

13. The therapeutic method according to claim 2 wherein the sigma receptor agonist compound is the N-cycloalkyl-benzylamine derivative represented by formula (3):

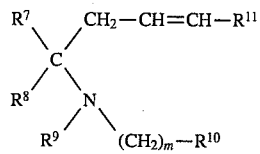

wherein $R^7$ represents phenyl which may be substituted by 1 to 3 members selected from halogen, lower alkyl, halo(lower) alkyl and lower alkoxy on the phenyl ring; $R^8$ represents lower alkyl; $R^9$ represents hydrogen or lower alkyl; $R^{10}$ represents cycloalkyl which may be substituted by lower alkyl or phenyl on the cycloalkyl ring; $R^{11}$ represents phenyl which may be substituted by 1 to 3 members selected from halogen and lower alkoxy on the phenyl ring; and m is equal to 1 or 2.

14. The therapeutic method according to claim 3 wherein the sigma receptor agonist compound is the N-cycloalkyl-benzylamine derivative represented by formula (3):

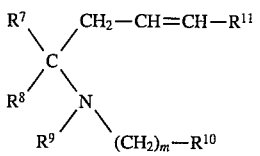

wherein $R^7$ represents phenyl which may be substituted by 1 to 3 members selected from halogen, lower alkyl, halo(lower) alkyl and lower alkoxy on the phenyl ring; $R^8$ represents lower alkyl; $R^9$ represents hydrogen or lower alkyl; $R^{10}$ represents cycloalkyl which may be substituted by lower alkyl or phenyl on the cycloalkyl ring; $R^{11}$ represents phenyl which may be substituted by 1 to 3 members selected from halogen and lower alkoxy on the phenyl ring; and m is equal to 1 or 2.

15. The therapeutic method according to claim 2 wherein the sigma receptor agonist compound is the carbostyril derivative represented by the following formula or a salt thereof:

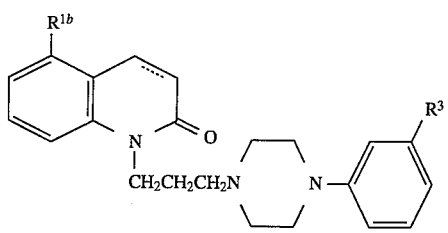

wherein $R^{1b}$ is selected from the group consisting of a methoxy, ethoxy, methyl and chloro group, $R^3$ is selected from the group consisting of a methoxy, chloro, bromo, nitro, hydroxyl and trifluoromethyl group; the carbon-carbon bond between the positions 3 and 4 of the carbostyril skeleton is a single bond or a double bond.

16. The therapeutic method according to claim 3 wherein the sigma receptor agonist compound is the carbostyril derivative represented by the following formula or a salt thereof:

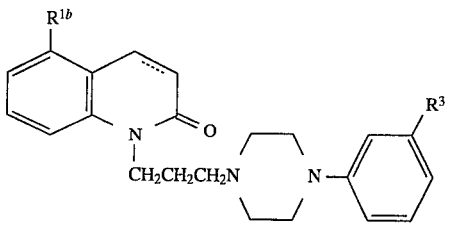

wherein $R^{1b}$ is selected from the group consisting of a methoxy, ethoxy, methyl and chloro group, $R^3$ is selected from the group consisting of a methoxy, chloro, bromo, nitro, hydroxyl and trifluoromethyl group; the carbon-carbon bond between the positions 3 and 4 of the carbostyril skeleton is a single bond or a double bond.

17. The therapeutic method according to claim 2 wherein the sigma receptor agonist compound is at least one compound selected from the group consisting of 2-allyl-5,9-dimethyl-2'-hydroxy-6,7-benzomorphan, 2-(3-methyl-2-butenyl)-5,9-dimethyl-2'-hydroxy-6,7-benzomorphan, 2-cyclopropylmethyl-5,9-dimethyl-2'-hydroxybenzomorphan, 2-methyl-5,9-dimethyl-2'-hydroxybenzomorphan, N,N'-di-(2-methylphenyl)guanidine, α-cinnamyl-N-cyclopropylmethyl-α-ethyl-N-methylbenzylamine, 5-methoxy-1-{3-[4-(3-chlorophenyl)-1-piperazinyl]propyl}-3,4-dihydrocarbostyril, 5-methoxy-1-{3-[4-(3-bromophenyl)-1-piperazinyl]propyl}-3,4-dihydrocarbostyril, 5-methoxy-1-{3-[4-(3-nitrophenyl)-1-piperazinyl]propyl}-3,4-dihydrocarbostyril, 5-ethoxy-1-{3-[4-(3-chlorophenyl)-1-piperazinyl]propyl}-3,4-dihydrocarbostyril, 5-chloro-1-{3-[4-(3-methoxyphenyl)-1-piperazinyl]propyl}-3,4-dihyrocarbostyril and 3-methoxy-N-methylmorphinan.

18. The therapeutic method according to claim 3 wherein the sigma receptor agonist compound is at least one compound selected from the group consisting of 2-allyl-5,9-dimethyl-2'-hydroxy-6,7-benzomorphan, 2-(3-methyl-2-butenyl)-5,9-dimethyl-2'-hydroxy-6,7-benzomorphan, 2-cyclopropylmethyl-5,9-dimethyl-2'-hydroxybenzomorphan, 2-methyl-5,9-dimethyl-2'-hydroxybenzomorphan, N,N'-di-(2-methylphenyl)guanidine, α-cinnamyl-N-cyclopropylmethyl-α-ethyl-N-methylbenzylamine, 5-methoxy-1-{3-[4-(3-chlorophenyl)-1-piperazinyl]propyl}-3,4-dihydrocarbostyril, 5-methoxy-1-{3-[4-(3-bromophenyl)-1-piperazinyl]propyl}-3,4-dihydrocarbostyril, 5-methoxy-1-{3-[4-(3-nitrophenyl)-1-piperazinyl]propyl}-3,4-dihydrocarbostyril, 5-ethoxy-1-{3-[4-(3-chlorophenyl)-1-piperazinyl]propyl}-3,4-dihydrocarbostyril, 5-chloro-1-{3-[4-(3-methoxyphenyl)-1-piperazinyl]propyl}-3,4-dihydrocarbostyril and 3-methoxy-N-methylmorphinan.

19. The therapeutic method according to claim 7, wherein the sigma receptor agonist compound is at least one compound selected from the group consisting of 5-Methoxy-1-{3-[4-(3-chlorophenyl)-1-piperazinyl]propyl}-3,4-dihydrocarbostyril, 5-Methoxy-1-{3-[4-(3-bromophenyl)-1-piperazinyl]propyl}-3,4-dihydrocarbostyril, 5-Methoxy-1-{3-[4-(3-nitrophenyl)-1-piperazinyl)propyl}-3,4-dihydrocarbostyril, 5-Ethoxy-1-{3-[4-(3-chlorophenyl)-1-piperazinyl)propyl}-3,4-dihydrocarbostyril, and 5-Chloro-1-{3-[4-(3-methoxyphenyl)-1-piperazinyl]propyl}-3,4-dihydrocarbostyril.

* * * * *